United States Patent [19]
Hsiao et al.

[11] Patent Number: 5,130,438
[45] Date of Patent: Jul. 14, 1992

[54] BIS-METHYLENE ETHER PYRIDINIUM COMPOUND PREPARATION

[75] Inventors: Luke Y. Y. Hsiao, Getzville, N.Y.; Hikmat A. Musallam, Damascus, Md.

[73] Assignee: The United States of America as represented by the Secretary of the Army, Washington, D.C.

[21] Appl. No.: 825,711

[22] Filed: Nov. 20, 1985

[51] Int. Cl.$^5$ .................... C07D 213/44; C07D 213/36
[52] U.S. Cl. ........................................ 546/262; 546/264
[58] Field of Search ................ 514/332; 546/262, 264, 546/266

[56] References Cited

U.S. PATENT DOCUMENTS 3,962,447  6/1976  Higuchi et al. .................. 514/332 X
4,128,651 12/1978  Hagedorn ............................ 514/332
4,352,810 10/1982  Benschop et al. .................. 514/332

OTHER PUBLICATIONS

Burness et al., "Bis(methylsulfonoxymethyl)ester" J. Org Chem vol. 42, No. 17, 1977, pp. 2910–2913.

Primary Examiner—John S. Maples
Attorney, Agent, or Firm—Anthony T. Lane; Werten F. W. Bellamy

[57] ABSTRACT

An illustrative embodiment of the invention substitutes solid, non-carcinogenic bis(methanesulfonoxymethyl) ether for bis-chloromethyl ether in a low temperature reaction of about 0°–5° C. for the production of bis-methylene ether pyridinium quaternary compounds. In this way, the production of important nerve agent antidotes (toxogonin, HI-6 and HGG-12) by a method of synthesis using the reactant bis-mesylmethyl ether, is carried out in appreciably greater safety.

4 Claims, No Drawings

BIS-METHYLENE ETHER PYRIDINIUM COMPOUND PREPARATION

BACKGROUND OF THE INVENTION

1. Field of the Invention

This invention relates to antidotes for nerve agents and, more particularly, to a method for preparing bis-methylene ether pyridinium quaternary compounds using bis-mesylmethyl ether reactant, and the like.

2. Prior Disclosure

Antidotes for nerve gas, or nerve agents, are of unquestionable importance. Safe and inexpensive production methods for these antidotes are, of course, equally significant.

Three of the more common nerve agent antidotes, toxogonin, HI-6 and HGG-12 require, in their manufacture, the use of bis-chloromethyl ether (BCME). Recently, however, BCME has been found to be such a potent carcinogen that it is no longer commercially available. For safe handling, human beings simply must not be exposed to this substance in any concentration, no matter how slight it may be.

In addition to this zero BCME exposure requirement, and the lack of any satisfactory analytical technique for detecting this substance in concentrations of less than one part per billion, BCME also is undesirable for a number of other reasons. BCME, for example, is a relatively volatile material. The customary reaction to prepare bis-methylene ether pyridinium quartenary compounds usually occurs at higher temperatures, in the range of °-60° C. Processing this dangerous and volatile material at these higher temperatures clearly is an hazardous undertaking.

Consequently, there is a need for a less volatile reagent for use in manufacturing nerve agent antidotes.

There is a further need to replace BCME in nerve agent antidote production with a non-carcinogenic material.

SUMMARY OF THE INVENTION

These and other difficulties that have characterized the prior art are overcome, to a great extent, through the practice of the invention. Illustratively, bis-mesylmethyl ether, which is non-carcinogenic, is substituted for the BCME in the production of bis-methylene ether pyridinium. A further advantage of the invention can be found in the fact that bis-mesylmethyl ether, when substituted for BCME in preparing bis-methylene ether pyridinium quaternary compounds, enjoys a low reaction temperature (0°-5° C.) and is in solid form.

Thus, there is provided in accordance with the invention an improved and substantially safer method for producing antidotes to organophosphorus compound nerve gasses and other nerve agents.

It should be further noted that there are applications for the invention well beyond use in nerve agent antidote production. Insecticides, for instance, would make use of the reagents and methods that characterize this invention.

DETAILED DESCRIPTION OF PREFERRED EMBODIMENT OF THE INVENTION

In accordance with the invention, bis-methylene ether pyridinium quaternary compounds are prepared using a specific sequence of reactions steps illustrated herein below, more specifically, the preparation of toxogonin, for example, in accordance with the principles of the invention, a prescribed sequence of steps has been developed. In this sequence, the reactants are combined in the following order:

1. acetyl chloride + methanesulfonic acid yields acetyl methanesulfonate
2. acetylmethanesulfonate + S-trioxane yields bis-(acetoxy)methane + bis(methanesulfonoxysethyl)ether
3. 4-pyridinealdoxime + bis(methanesulfonoxymethyl) ether yields 1,1'-[oxybis(methylene)]bis[4-(hydroxyimino) methyl]-pyridinium dimethanesulfonate
4. 1,140 [oxybis(methylene)]bis[4-(hydroxyimino)-methyl]pyridinium dimethanesulfonate is applied to a column of chloride ion exchange resin and separating the corresponding dichloride derivative referred to herein as toxogonin.

Applicants novel process is directed to the preparation of bis-methylene ether pyridinium quaternary composition 5 represented by the formula:

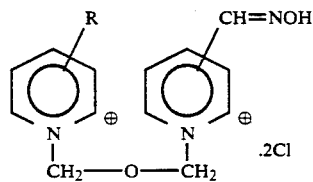

wherein R is selected from the group consisting essentially of

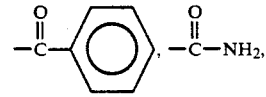

and —CH=NOH, comprising the steps of a. reacting bis(methanesulfonoxymethyl) ether with a pyridineal compound having the formula

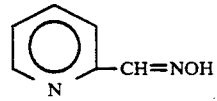

at a temperature of about 0° to 5° C. and b. applying product of step a. to a column of chloride ion exchange resin and separating the said quaternary composition.

The preferred compositions prepared according to the process of this invention are made either when (1) the pyridineal compound of step a. is

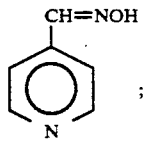

or (2) the pyridineal compound of step a. is

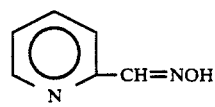

and isonicotinamide is subsequently added to the reaction mixture of stp a.; or (3) the pyridineal compound of step a. is

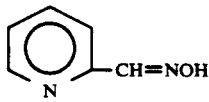

and 3-benzoylpyridine is subsequently added to the reaction mixture of step a. Following the procedures designated herein above as "(1)", "(2)", and "(3)" results in the preparation of 1,1'Oxybis(methylene) bis-4-(hydroxyimino)methyl pyridinium dichloride; 1-(2-Hydroxyimino-methyl-1-pyridino)-3-(40carbamoyl-1-pyridino)-2-oxapropane dichloride; and 1-(2-Hydroxyiminomethyl-1-pyridino)-3-(3-benzoyl-1-pyridino)-2-oxapropane dichloride, respectively.

EXAMPLE 1

Acetyl methanesulfonate (3)

$$CH_3CCl + CH_3S-OH \longrightarrow CH_3S-O-CCH_3$$

(with O, O, O, O above/below as drawn)

1           2                           3

| 1 | 2 | Solvent | Temp. | 3 |
|---|---|---|---|---|
| 100 g | 48 g | none | reflux | 43.2 g (63%) (after distillation) |
| 200 g | 96.1 g | none | reflux | 137.8 g (100%) (crude) |
| 200 g | 96.1 g | none | reflux | 128.7 g (93%) (crude) |
| 200 g | 96.1 g | none | reflux | 141.5 g (100%) (crude) |

A stirred mixture of acetyl chloride (1) (500 g, 6.37 mol) and methanesulfonic acid (2) (240 g, 2.50 mol) under a moisture free argon atmosphere was heated at reflux for 20 hours. Evolution of HCl gas was observed. The reaction mixture was cooled and concentrated in vacuo to give 341 g (99%) of product as a red oil. Additional reactions of the same size were carried out to give a total of 3,730 g of product suitable for further transformation.

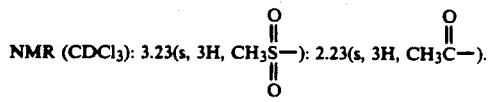

NMR (CDCl$_3$): 3.23(s, 3H, CH$_3$S—): 2.23(s, 3H, CH$_3$C—).

EXAMPLE 2

Bis(methanesulfonoxymethyl)esther (5)

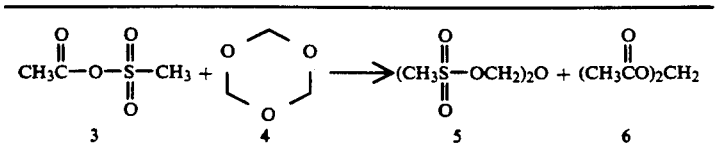

| 3 | 4 | CH$_3$SO$_3$H | Solvent | Temp. | 5 |
|---|---|---|---|---|---|
| 13.8 g | 4.5 g | none | neat | 85-90° | 6.0 g (26%) |
| 63.1 g | 41.5 g | 1.6 mL | neat | 85-90° | 78.8 g (crude product) |
| 137.8 g | 96.1 g | 3.5 mL | neat | 85-90° | 159 g (crude product) |
| 68 g | 24 g | 1.7 mL | neat | 85-90° | 81 g (crude product) |
| 27.8 g | 23.2 g | 0.7 mL | neat | 85-90° | 32 g (crude product) |
| 140 g | 117.3 g | 35 mL | neat | 90° | 156.2 g (crude product) |
| 20 g | 13.3 g | 0.3 mL | CH$_3$CN | 65° | poor yield of 5 |

To stirred acetyl methanesulfonate (3) (680 g, 4.92 mol) under an argon atmosphere at 10° was added s-trioxane (4) (244 g, 2.70 mol) portionwise over 15 minutes, while maintaining the temperature of the reaction mixture at 15°-25°. Upon completion of the addition, the mixture was stirred at room temperature for 15 minutes, then slowly heated to 90° over a 1 hour period. When the temperature reached ~30°, the argon inlet was replaced with a distillation head and a vacuum (0.5-1.0 torr) was applied to the reaction with a high capacity vacuum pump. The reaction by-product, bis-(acetoxy)methane (6), was collected as the mixture was heated at 90°. When the collection of distillate ceased (after ~3 hours), the reaction mixture was cooled and the product used immediately in the next step without further isolation or purification.

EXAMPLE 3

1,1'-[Oxybis(methylene b s (4-(hydroxyimino)methyl]pyridinium dimethanesulfonate (8)

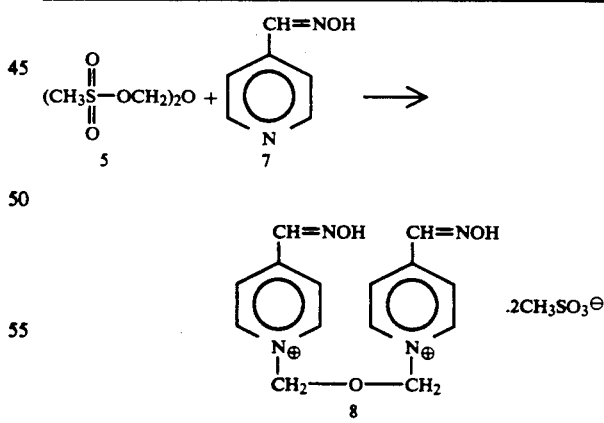

| 5 | 7 | Solvent | Temp. | 8 |
|---|---|---|---|---|
| 14.5 g | 11.4 g | CH$_3$CN | 24° | 6.5 g (22%) |
| 101.5 g | 79.8 g | CH$_3$CN | 24° | 44 g (28%) |

To a stirred suspension of 4-pyridinealdoxime (79.8 g, 0.653 mol) in dry acetonitrile (400 mL) under an argon atmosphere at room temperature was added a solution of bis(methanesulfonoxymethyl)ether (101.5 g, 0.433 mol) in acetonitrile (70 mL) dropwise during 30 minutes. The suspension became a clear brown solution and an exotherm to 45° was observed. Upon completion of the addition, the reaction mixture was stirred at room temperature for 20 hours. The solid which precipitated was collected on a filter, washed with EtOH (250 mL), and dried to constant weight in vacuo at 55° to give 65 g of product as a tan solid. This material was recrystallized from MeOH (1.2 L) to give 39.1 g of purified product. Concentration of the mother liquor yielded another 5.0 g of product, which was combined with the first crop to give 44.1 g (28%) of purified product; mp 208°–210°. A 10.0 g sample of this material was dissolved in $H_2O$ (40 mL) and concentrated. The oily residue was triturated in EtOH (40 mL) and the resulting white solid was collected to give 9.1 g of analytically pure product; mp 211–213°.

To a stirred suspension of 4-pyridinealdoxime (7) (439 g, 3.50 mol) in dry acetonitrile (2.2 L) under an argon atmosphere at 5°–10° was added a solution of freshly prepared bis(methanesulfonoxymethyl)ether (5) (561 g, 2.40 mol) (Note 1) in dry THF (390 mL) as a thin stream during 30 minutes, while maintaining the temperature of the reaction mixture at 5°–10°. Upon completion of the addition, a solid slowly precipitated out of the resulting cloudy brown solution. The suspension was stirred at room temperature for 18 hours. The solid was collected on a filter, washed with acetonitrile (200 mL), partially dried, then recrystallized from MeOH (14 L) to give 480 g (56%) (Note 2) of product as a light brown solid. Additional reactions were carried out to give a total of 2,595 g of equivalent material. A 1,006 g portion of this material was recrystallized from EtOH/$H_2O$ (10 L:1.2 L) (charcoal) to give 864 g (85% recovery) of purified product as a light tan solid; mp 211°–214° (d) (Note 3). The remaining material was recrystallized in two portions in the same manner to give a total of 2,154 g of product suitable for further transformation.

| Anal. | C | H | N | O | S |
|---|---|---|---|---|---|
| Calc'd. for $C_{16}H_{22}N_4O_9S_2$ | 40.16 | 4.63 | 11.71 | 30.09 | 13.40 |
| Found | 40.20 | 4.74 | 11.85 | 29.73 | 13.40 |

Spectral Data:
Infrared (Nujol)
Major bands: 3130, 3050, 2960, 2920, 2860, 2780, 1640, 1610, 1515, 1490, 1460, 1420, 1380, 1320, 1300, 1225, 1200, 1170, 1150, 1090, 1030, 1000, 850, 795, 765 cm$^{-1}$.
Ultraviolet ($H_2O$);
$\lambda_{max}$ 352 nm (log$_\epsilon$3.584); 285 nm (4.512); $\lambda_{shoulder}$ 216 nm (4.095).
Nuclear Magnetic Resonance ($D_2O$); δ9.05 (d, 4H, J=7 Hz, aromatic); 8.30 (s, 2H, 2 CH=N—); 8.25 (d, 4H, J=7 Hz, aromatic); 6.20 (s, 4H, 2 —$CH_2O$); 2.85

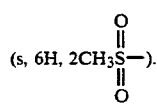

(s, 6H, 2CH$_3$S—).

EXAMPLE 4

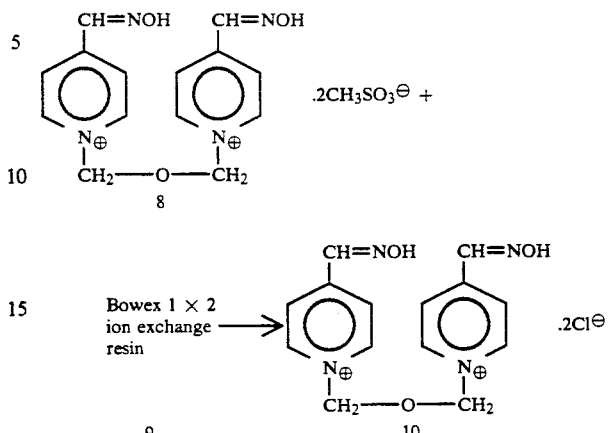

An aqueous solution (600 mL) of 1,1'-[oxybis(methylene)]-bis[4-(hydroxyimino)methyl]pyridinium dimethanesulfonate (8) (350 g, 0731 mol) was applied to a column of ion exchange resin (9) (4 L of Dowex 1×2, Cl$^-$ form). The solution was held on the column for 2 hours, then eluted with $H_2O$. Those fractions containing product (Note 4) were combined and concentrated in vacuo to a small volume (~500 mL). EtOH (~2 L) was added until a solid began to precipitate. Most of the $H_2O$ was removed by co-evaporation in vacuo with portions of EtOH (3×2 L). The solid was collected from the resulting suspension of ~1.5 L, then washed with EtOH (4×500 mL) and dried to constant weight in vacuo at 50° to give 240 g (91%) of toxogonin as a yellow solid. Additional columns of the same size were carried out to give a total of 1,418 g of equivalent material. A 676 g portion of this material was recrystallized from EtOH/$H_2O$ (6.75 L:1.5 L) (charcoal) to give 526 g (78% recovery) of purified toxogonin (10) as a light tan solid (Note 5). The remaining material was recrystallized in the same manner to give a total of 1,085 g of analytically pure toxogonin; mp 191°–192° (d).

| Anal. | C | H | N | Cl | O |
|---|---|---|---|---|---|
| Calc'd. for $C_{14}H_{16}N_4O_3C_{l2}$ | 46.81 | 4.49 | 15.60 | 19.74 | 13.36 |
| Found | 46.83 | 4.58 | 15.49 | 19.67 | 13.51 |

Spectral Data:
Infrared (Nujol)
Major bands: 3050, 2920, 2840, 2720, 1640, 1605, 1580, 1560, 1510, 1445, 1370, 1300, 1160, 1085, 985, 840, 780 cm$^{-1}$.
Ultraviolet ($H_2O$): $\lambda_{max}$ 285 nm (log$_\epsilon$4.531); $\lambda_{shoulder}$ 215 nm (4.040).
Nuclear Magnetic Resonance ($D_2O$): δ 9.05 (d, 4H, J=8 Hz, aromatic H); 8.30 (s, 2H, —CH=N—); 8.25 (d, 4H, J=8 Hz, aromatic H); 6.15 (s, 4H, —$CH_2O$—); 4.70 (s, 2H, HOD).
Chromatography:

| Thin Layer Chromatography Cellulose, (Analtech Uniplate MN300F Glass Plates) ||
|---|---|
| Solvent System | R$_f$Value |
| 1. n-BuOH, HOAc, $H_2O$ (5:1:2) | 0.50 |

Detection: Ultraviolet light
Quantity Spotted: 20 gamma
Results: A major spot and a trace impurity at $R_f = 0.30$ were observed.

| (Silica gel, E. Merck 60F-254 Glass Plates) | |
|---|---|
| Solvent System | $R_f$ Value |
| 1. n-BuOH, HOAc, H$_2$O (5:1:2) | 0.09 |

Detection: Ultraviolet light
Quantity Spotted: 20 gamma
Results: A single spot and a trace baseline were observed.
Notes:
1. The amount of the bis ether (561 g) assumes a theoretical yield of the previous reaction (step b). It was not weighed or other wise manipulated other than to dissolve it in THF and transfer it immediately to an addition funnel under argon. Rather this amount was only used as a means of calculating the amount of 4-pyridinealdoxime to use in step c and is in no way indicative of the actual yield of the bis ether in step b.
2. This is a combined yield of steps b and c and is based on the amount of 4-pyridinealdoxime.
3. The color of the dimethanesulfonate salt after the contained product showed a strong absorption of the ultraviolet light.
5. As with the dimethanesulfonate salt, the color of the crude toxogonin varied from lot to lot from pale yellow to dark greenish-gold. Recrystallization from EtOH/H$_2$O using charcoal again yielded a uniformly light tan solid.

EXAMPLE 5

To produce the antidote HGG-12 in the absence of the volatile and carcinogluci BCME, a further sequence has been developed.
1. Bis(methanesulfonoxymethyl)ester + 2-pyridinoaldoxime + 3-benzoylpyridine yield 1,1[oxybis(methylene)]-bis[3-benzoyl] pyridinium dimethanesulfonate
2. 1,1[oxybis(methylene)]-bis [-3-benzoyl] pyridinium dimethanesulfonate + ion exchange resin to eliminate the chloride yield 1-(2-hydroxyiminomethyl-1-pyridino)-3-(3-benzoyl-1-pyridino)-2-oxapropane dichloride.

A specific example of a procedure to manufacture the antidote HGG-12 is described below.

HGG-12

1-(2-Hydroxyiminomethyl-1-pyridino)-3-(3-benzoyl-1-pyridino)-2-oxapropane dimethanesulfonate (15)

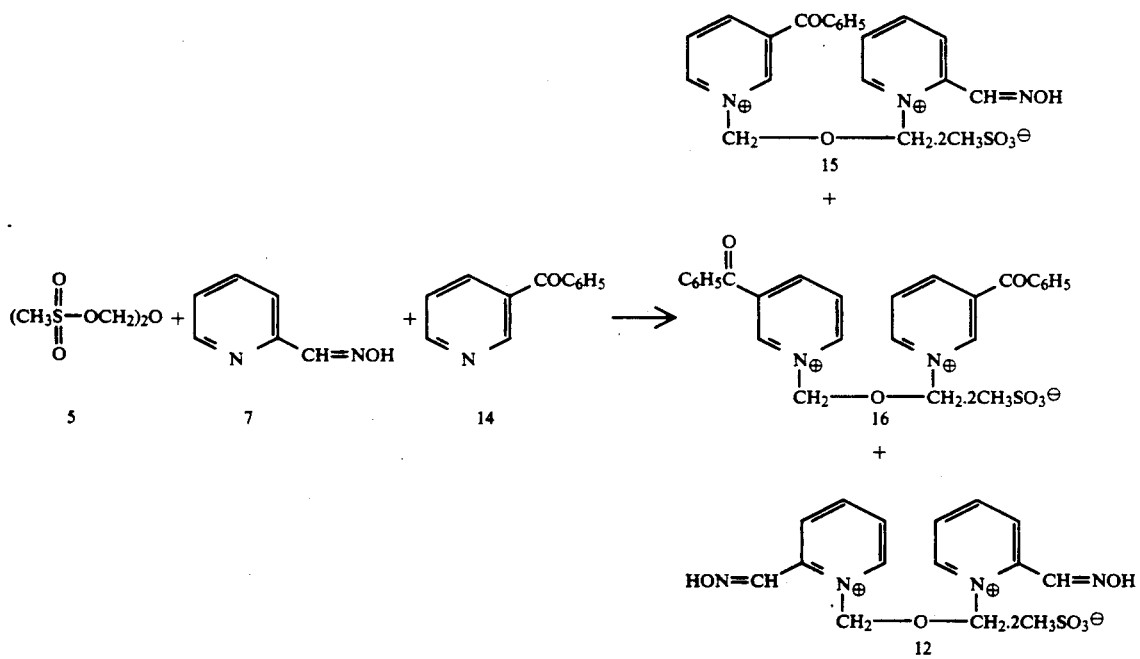

| Run | 5 | 7 | 14 | Time (h) Initial | Total | Temp. | Unpurified Product Yield | % |
|---|---|---|---|---|---|---|---|---|
| 1 | 157.1 g | 81.8 g | 122.8 g | 2 | 20 | 5–25° | 261 g | (72%) |
| 2 | 115 g | 51 g | 76.3 g | 8 | 20 | 5–25° | 35.6 g | (14%) |
| 3 | 90.4 g | 45 g | 67 g | 8 | 20 | 5–25° | 50 g | (24%) |
| 4 | 109.5 g | 54 g | 81 g | 2 | 20 | 5–25° | no product formed | |

MeOH recrystallization varied from lot to lot from dark to light brown. The EtOH/H$_2$O recrystallization using charcoal gave a good recovery of a uniformly light tan solid.
4. In order to determine whether or not a fraction contained product, it was spotted on a TLC plate and examined under ultraviolet light. Those spots which Bis(methanesulfonoxymethyl) ether (90.4 g, 0.386 mol) was dissolved in dry acetonitrile (640 mL) under argon and cooled to 0.5°. A solution of 2-pyridinoaldoxime (45 g, 0.368 mol) in 1250 mL of acetonitrile was added, dropwise, over 3 hours. The reaction mixture was continually stirred at room temperature for 5 hours. A solution of 3-benzoylpyridine (67 g, 0.366 mol) in 150 mL of acetonitrile was added over 30 minutes. The reaction mixture was stirred at room temperature overnight. The brown residue was separated by decantation and stirred with 800 mL of EtOH. The insoluble tan material was removed to give 24.5 g of 1,1,-[oxybis(methylene)]-bis[3-benzoyl]pyridinium dimethanesulfonate (16). The filtrate was spin-evaporated in vacuo to give unpurified product (50 g, yield 24%. NMR showed that this material contained about 50% of desired product (15). This material was converted to chloride salt, without further transformation.

Note: No desired product was formed when 3-benzoylpyridine was added first followed by 2-pyridinealdoxime.

HGG-12;
1-(2-Hydroxyiminomethyl-1-pyridino)-3-(3-benzoyl-1-pyridino)-2-oxapropane dichloride (17)

$$C_6H_5-C(=O)-\text{pyridinium}-CH_2-O-CH_2-\text{pyridinium}-CH=NOH \cdot 2CH_3SO_3^{\ominus}$$

15

$$\xrightarrow{\text{ion exchange resin, Cl}^{\ominus}}$$

$$C_6H_5-C(=O)-\text{pyridinium}-CH_2-O-CH_2-\text{pyridinium}-CH=NOH \cdot 2Cl^{\ominus}$$

17

| Run | 15 | Resin mL | 17 (yield) |
|---|---|---|---|
| 1 | 60.0 g | 500 mL | No product isolated |
| 2 | 59.2 g | 500 mL | No product isolated |
| 3 | 10.0 g | 100 mL | No product isolated |
| 4 | 193.0 g | 2500 mL | No product isolated |
| 5 | 35.6 g | 500 mL | 8.3 g |
| 6 | 50.0 g | 600 mL | 8.7 g |

The unpurified methanesulfonate salt (15) (35.6 g, 0.066 mol) was dissolved in $H_2O$ (50 mL) and applied to an ion exchange resin (Cl$^-$ form, 500 mL). The column was eluted with EtOH-$H_2O$ (1:1) and the appropriate fractions were combined and spin-evaporated in vacuo to give 27.9 g of a brown foaming solid. The material was dissolved in EtOH (300 mL) and the insolubles were removed by filtration. The filtrate was treated with charcoal, filtered and concentrated to about 100 mL and cooled. The white crystals were collected to give 8.3 g of desired product. Additional runs were carried out to give 8.7 g. Both materials were combined then recrystallized from hot EtOH (300 mL) to give 14.1 g (83% recovery); mp,. 120°-125° (d).

| Anal. | C | H | N | Cl | O |
|---|---|---|---|---|---|
| Calc'd. for $C_{20}H_{19}Cl_2N_3O$ .1.11$C_2H_5OH.O.55H_2O$ | 55.44 | 5.60 | 8.73 | 14.73 | 15.48 |
| Found | 55.68 | 5.42 | 8.55 | 14.51 | 15.95 |

Spectral Data:
Infrared (Nujol)
Major bands: 3380, 3140, 3080, 2960, 2920, 2860, 1670, 1630, 1595, 1575, 1500, 1465, 1450, 1380, 1330, 1310, 1295, 1270, 1190, 1170, 1150, 1140, 1110, 1040, 1030, 970, 955, 890, 870, 840, 805, 710, 690 cm$^{-1}$.

Ultraviolet ($H_2O$): $\lambda_{max}$ 295 nm (log $\epsilon$4,145); 270 nm (4.168).

Nuclear Magnetic Resonance ($D_2O$): $\delta$9.50-7.10 nm, 14H, aromatic and methine protons); 6.42 (s, 2H, —C$\underline{H}_2$—); 6.35 (s, 2H, —C$\underline{H}_2$—); 4.62 (s, HOD); 3.60 (q, —C$\underline{H}_2$—CH$_3$); 1.20 (t, —CH$_2$—C$\underline{H}_3$).

Chromatography:

| Thin Layer Chromatography (Silica Gel, E. Merck 60 F-254 Glass Plates) | |
|---|---|
| Solvent System | $R_f$ Value |
| 1. n-BuOH, HOAc, $H_2O$ (5:1:2) | 0.08 |

Detection: ultraviolet light
Results: A major spot (product) and two trace spots at $R_f$=0.83 (3-benzoylpyridine), $R_f$=0.58 (2-pyridinealdoxime). We have not eliminated the possibility that the apparent impurities actually represent decomposition products caused by this TLC system.

EXAMPLE 6

In order to produce HI-6, in accordance with the principles the invention, the following procedures has been developed:

1. Acetyl methanesulfonate + S - trioxane yield bis-(acetoxy) methane + bis (methane sulfonoxymethyl)ether 2. Bis(methanesulfonoxymethyl)ether + 2-pyridinealdoxime + isonicotinamide yield 1-(2-hydroxyiminomethyl-1-pyridino)-3-(4-carbamoyl-1-pyridino-2-oxapropane dimethanesulfonate A specific example of a procedure to manufacture the antidote HI-6 is described below.

HI-6

Purified bis(methanesulfonoxymethyl)ether $$CH_3S(=O)_2-O-C(=O)CH_3 + \text{trioxane} \longrightarrow$$
3     4

$$(CH_3S(=O)_2-OCH_2)_2O + (CH_3CO)_2CH_2$$
5     6

| 3 | 4 | Solvent | Temp. | 5 |
|---|---|---|---|---|
| 295 g | 106 g | none | 90° | 100 g (brown solid) 95% pure |

To cold (5°), stirred acetyl methanesulfonate (3) (295 g, 2,14 mol) was added s-trioxane (4) (106 g, 1.18 mol) portonwise during 30 minutes. Upon completion of the addition, the reaction mixture was stirred at room temperature for 1 hour, then slowly heated to 90°. When the temperature reached ~30°, a vacuum (0.5-1.0 torr) was applied to remove the reaction by-product, bis- (acetoxy)methane (6). After heating at 90° for 3 hours, the reaction mixture was cooled, diluted with THF (140 mL), treated with decoloring carbon, and filtered quickly under argon. Et₂O (100 mL) was added to the filtrate and the solution was stored in the freezer overnight. The precipitated brown solid was collected under argon in a glove bag, and dried in vacuo at room temperature for 1 hour to give 100 g (44%) of purified product (5). This material was 95% pure as determined by NMR.

EXAMPLE 7

1-(2-Hydroxyiminomethyl-1-pyridino)-3-(4-carbamoyl-1-pyridino)-2-oxapropane dimethanesulfonate (27)

stirred at room temperature overnight (16 hours). The resulting gummy brown material which precipitated was collected by decantation and then stirred with 500 mL of ethanol. The insoluble tan solid was collected and dried in vacuo to give 71.8 g of crude product (47%). This material was suspended in 1440 mL of MeOH and stirred for 30 minutes. The insoluble brown material was removed, and the filtrate was concentrated to give 53.0 g of residue. A 20 g portion was dissolved in 350 mL of MeOH, treated with decoloring carbon, then filtered. The filtrate was triturated with 50 mL of EtOH and chilled in the freezer overnight. The resulting white crystals were collected, and dried in vacuo at 50°–60° to give 6.4 g of product; mp, 161°–164° (d).

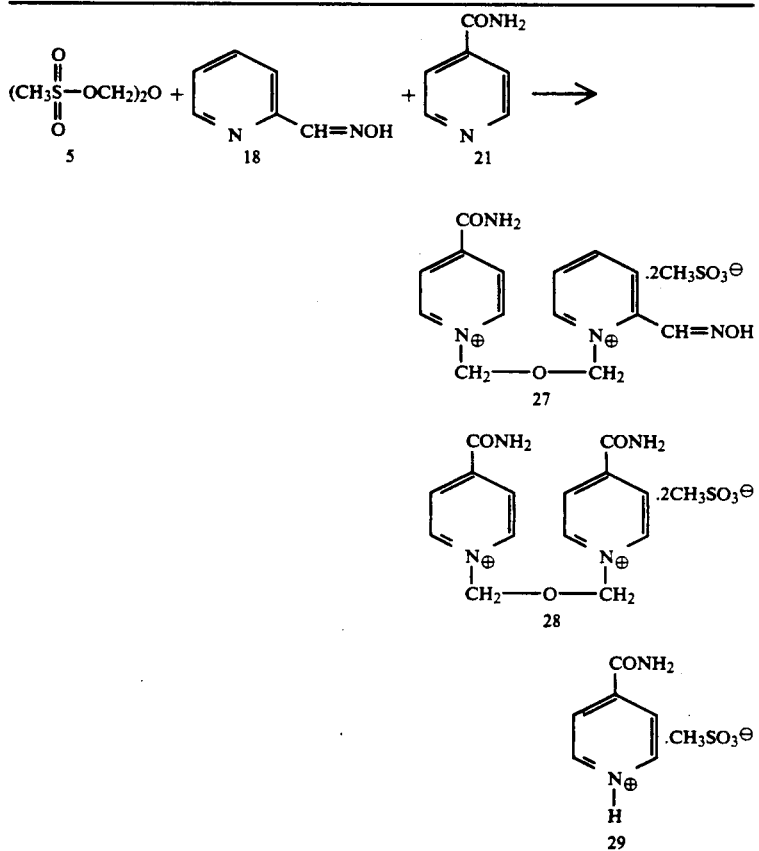

| 5 Solvent | 18 Solvent | 21 Solvent | Temp. | Time | 27, 28, 29 |
|---|---|---|---|---|---|
| 9.2 g THF | 4.8 g CHCN | 4.8 g CH₃CN | 0-5° | 18 hr | 5.3 g (28%) |
| 225 g THF | 11.7 g THF | 11.7 g CH₃CN | 0-5° | 18 hr | 18.1 g (39%) |
| 12.9 g CH₃CN | 6.7 g CH₃CN | 6.7 g none | 0-5° | 18 hr | 8.8 g (33%) |
| 11.6 g CH₃CN | 6.0 g CH₃CN | 6.0 g none | 0-5° | 18 hr | 10.0 g (42%) |
| 8.1 g CH₃CN | 4.1 g none | 4.1 g none | 0-5° | 18 hr | no product |
| 74.3 g CH₃CN | 38.7 g CH₃CN | 38.7 g none | 0-5° | 18 hr | 71.8 g (47%) |
| 67.5 g CH₃CN | 35.2 g CH₃CN | 35.2 g none | 0-5° | 18 hr | 49.5 g (36%) |
| 15.6 g CH₃CN | 8.1 g CH₃CN | 8.1 g DMF | 0-5° | 18 hr | 6.5 g (20%) |
| 150 g CH₃CN | 78 g CH₃CN | 78 g none | 0-5° | 18 hr | 144 g (65%) |
| 65 g CH₃CN | 33.9 g CH₃CN | 33.9 g none | 0-5° | 18 hr | 64.3 g (48%) |
| 35.9 g CH₃CN | 18.7 g CH₃CN | 18.7 g DMF | 0-5° | 18 hr | 25 g (34%) |

To a solution of purified bis(methanesulfonoxymethyl)ester (74.3 g, 0.317 mol) (5) in 500 mL of dry CH₃CN (0°–5° under argon) was added a solution of 2-pyridinealdoxime (38.7 g, 0.317 mol) (18) in 1 L of CH₃CN over 2.5 hours. After the addition was completed, the reaction mixture was stirred for 6 hours. Isonicotinamide (38.7 g, 0.317 mol) (21) was added, portionwise, during 20 minutes. The solution was

| Anal. | C | H | N | O | S |
|---|---|---|---|---|---|
| Calc'd. for C₁₆H₂₂N₄O₉S₂ | 40.16 | 4.63 | 11.71 | 30.09 | 13.40 |
| Found | 39.83 | 4.84 | 11.56 | 30.21 | 13.51 |

Spectral Data:

Infrared (Nujol)

Major bands: 3340, 3160, 3120, 3060, 2960, 2920, 2860, 2760, 1700, 1630, 1600, 1570, 1500, 1400, 1380, 1330, 1260, 1240, 1190, 1150, 1130, 1100, 1020, 960, 855, 810, 765, 715 cm$^{-1}$.

Ultraviolet (H$_2$O): $\lambda_{max}$352 nm (log$_\epsilon$3.073); 300 nm (4.046); 271 nm (3.995); 218 nm (4.221).

Nuclear Magnetic Resonance (D$_2$O): δ 9.40–7.80 (m, 9H, aromatic and methine proton); 6.40 (s, 2H, —CH$_2$—); 6.26 (s, 2H, —CH$_2$—); 2.75

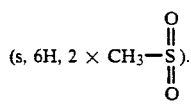

(s, 6H, 2 × CH$_3$—S—).

1-(2-Hydroxyiminomethyl-1-pyridino)-3-(4-carbamoyl-1-pyridino)-2-oxapropane dimethanesulfonate (9)

isonicotinamide (897 g, 7.35 mol) was added in portions over 1.5 hours at 0°. The reaction was allowed to warm slowly to room temperature and stirring was continued overnight. The liquid was decanted, and the residue was triturated with EtOH (10 L). After stirring for 3 hours, the solid was collected by filtration and dried to constant weight in vacuo at 50° to yield 1485 g (43%) of unpurified product as a mixture of (9) (10), (11), and (12). Multiple fractional crystallizations from CH$_3$OH, H$_2$O, and EtOH-H$_2$O afforded 280 g (63% recovery) of product suitable for conversion to dichloride salt on ion exchange resin. The total yield was 880 g of pure HI-6 dimethanesulfonate salt.

In accordance with the invention, there is a further distinctive step that converts the results product (9) from the preceding step into the desired HI-6. Thus, 1,1'[oxybis(methylene)]bis[2-hydroxyimino)methyl]-pyridinium dimethanesulfonate + ion exchange column yield 1-(2-hydroxyiminomethyl-1-pyridino)-3-(4-car-

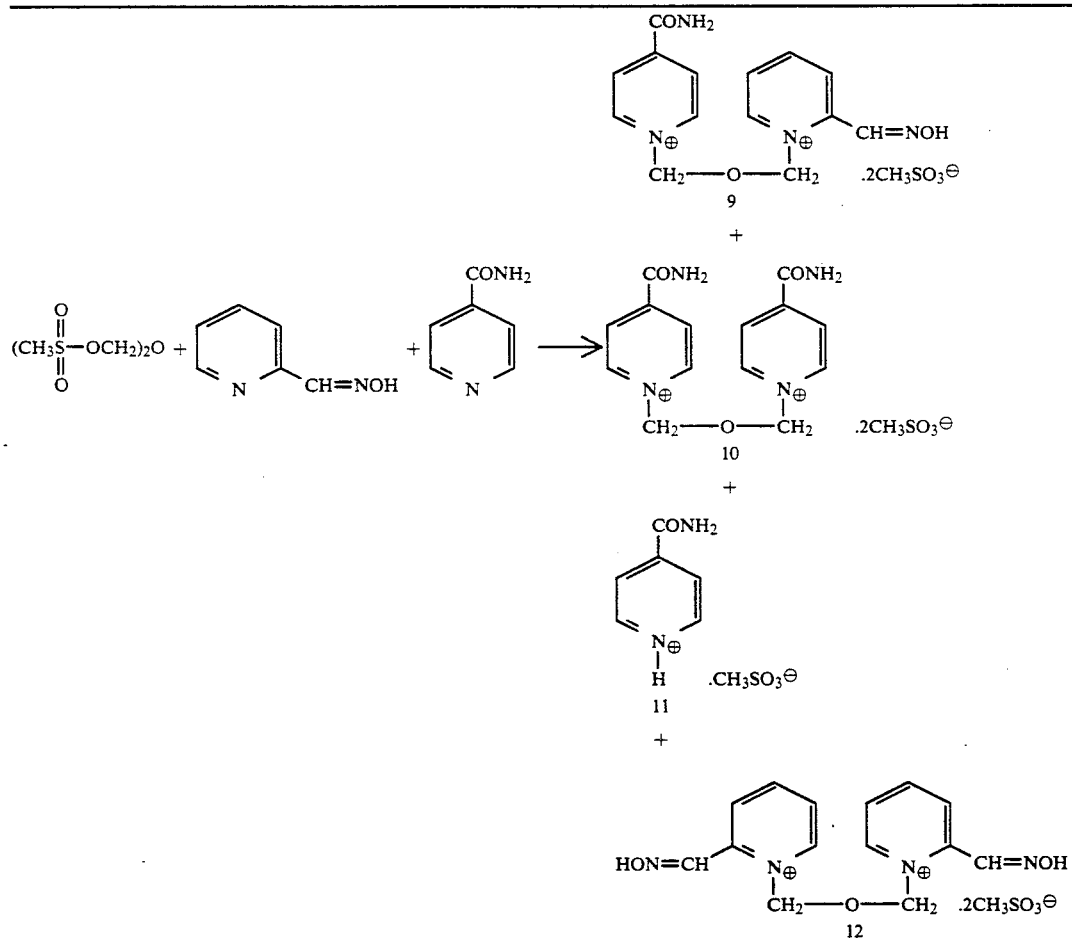

| Run | Time (h) 5 | 7 | 8 | Initial | Total | Temp. | Unpurified Product Yield | Ratio (9:10:11:12) |
|---|---|---|---|---|---|---|---|---|
| 1 | 1221.4 g | 635.8 g | 635.8 g | 9 | 22 | 0–25° | 927 g (39%) | 6:3:7:4 |
| 2 | 1721.0 g | 897.0 g | 897.0 g | 9 | 22 | 0–25° | 1485 g (43%) | 6:3:10:1 |
| 3 | 2117.0 g | 1103 g | 1103 g | 13 | 28 | 0–25° | 1643 g (38%) | 6:3:10:1 |

To a stirred solution of bis(methanesulfonoxymethyl)ether (5) (1721 g, 7.35 p;) in dry CH$_3$CN (12 L) was added 2-pyridinealdoxime (897 g, 7.35 mol) in dry CH$_3$CN (23 L) at 0° during 6.5 hours. The reaction was stirred at room temperature for 3 hours then the bamoyl-1-pyridino)-2-oxapropane dichloride monohydrate.

A specific example of this process is as follows:

HI-6

1-(2-Hydroxyiminomethyl-1-pyridino)-3-(4-carbamoyl-1-pyridino(-2-oxapropane dichloride monohydrate (30)

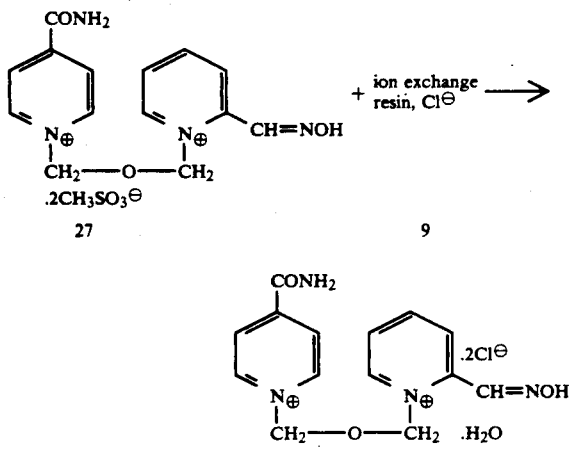

A solution of 1,1'-oxybis(methylene) bis 2-hydroxymino)methyl pyridinium dimethanesulfonate (25.1 g) (27) in 40 mL of water was applied to an ion exchange column (300 mL of Dowex 1×2, Cl⊖form). The solution was held on the column for 45 minutes then eluted with water. The fractions containing the product were combined, and concentrated in vacuo. The residue was dried azeotropically with ethanol (100 mL), triturated with 150 mL of EtOH, and the solid was collected and dried in vacu to give 16.6 g. This material was dissolved in a solution of methanol (1000 mL) and water (30 mL) and water (30 mL), treated with decolorizing charcoal, then filtered. The filtrate was cooled, and the precipitate (2.2 g) which formed was removed by filtration. The filtrate was concentrated to about 50 mL then cooled. The white solid (13 g), recovered from the solution, was recrystallized from water (20 mL) and ethanol (75 mL) to give 7.9 g of pure product; mp 145°–147° (d).

| Anal. | C | H | N | Cl | O |
|---|---|---|---|---|---|
| Calc'd. for $C_{14}H_{16}N_4O_3Cl_2.H_2O$ | 44.58 | 4.81 | 14.85 | 18.80 | 16.97 |
| Found | 44.59 | 4.78 | 14.87 | 18.98 | 16.77 |

Spectral Data:
Infrared (Nujol)

Major bands: 3320, 3260, 3180, 3080, 3030, 2960, 2920, 2860, 2780, 1680, 1640, 1625, 1570, 1490, 1460, 1440, 1395, 1380, 1330, 1260, 1240, 1190, 1160, 1140, 1120, 1095, 1080, 1070, 1010, 960, 860, 810, 780, 710 $cm^{-1}$ Ultraviolet ($H_2O$): $\lambda_{max}$ 350 nm ($log_e$3.093); 300 nm (4.018); 270 nm (3.966); 218 nm (4.181).

Nuclear Magnetic Resonance: δ 9.40–7.70 (m, 9H, aromatic and methine); 6.45 (s, 2h, —$CH_2$—); 6.32 (s, 2H, —$CH_2$—).

This process was repeated:

1-(2-Hydroxyiminomethyl-1-pyridino)-3-(4-carbamoyl-1-pyridino)-2-oxapropane dichloride monohydrate (13) (HI-6)

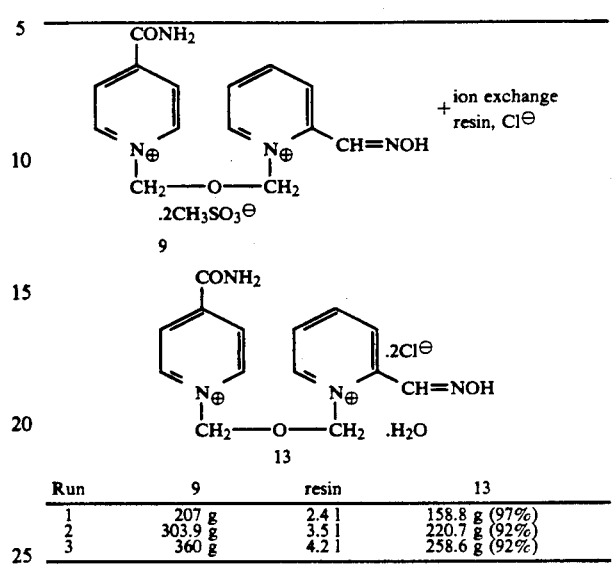

| Run | 9 | resin | 13 |
|---|---|---|---|
| 1 | 207 g | 2.4 l | 158.8 g (97%) |
| 2 | 303.9 g | 3.5 l | 220.7 g (92%) |
| 3 | 360 g | 4.2 l | 258.6 g (92%) |

A solution of 1,1'-[oxybis(methylene)]bis [bis[2-hydroxyimino)-methyl]pyridinium dimethanesulfonate (303.0 g, 0.635 mol) in 520 mL of water was applied to an ion exchange column (3.5 L of Dowex 1×2, Cl⁻form). The solution was held on the column for 45 minutes then eluted with water. The fractions containing the product was combined, then concentrated in vacuo. The residue was dried azeotropically with ethanol (100 mL) then triturated with 150 mL of EtOH. The insoluble solid was collected and dried in vacuo to give 220.7 g (92%). The total yield was 638 g of HI-6.

Thus, the invention provide a safe procedure for the manufacture of nerve agent antidotes without using carcinogenic raw materials. Some minor variations to the procedure and materials described above render the invention adaptable to insecticide production. These variations, being within the ability of a skilled artisan, also are within the scope of the claimed invention.

Utility

The bis-methylene ether pyridinium quaternary compounds prepared according to the process of this invention are useful as nerve agent antidotes. More specifically, evidence indicates that these compounds demonstrate activity against nerve gases or nerve agents.

We claim:
1. A method for producing 1-(2-Hydroxyiminomethyl-1-pyridino)-3-(4-carbamoyl-1-pyridino)- 2-oxapropane dichloride mono hydrate comprising the steps of
   a. reacting bis(methylsulfonoxymethyl)ether with pyridino-2-aldoxime at a temperature of about 0° to 5° C.;
   b. adding isonicotinamide with the reaction product of step a.; and
   c. applying the product of step b. to a column of chloride ion exchange resin and separating the said quaternary composition.
2. The composition prepared according to the process of claim 1.
3. A method for producing 1-(2-Hydroxyiminomethyl-1-pyridino)-3-(3-benzoyl-1-pyridino)-2-oxapropane dichloride comprising the steps of
   a. reacting bis(methylsulfonoxymethyl)ether with 3-benzoylpyridine at about −35° C.;
   b. reacting the reaction product of step a. with pyridine-2-aldoximine; and
   c. applying the product of step b. to a column of chloride ion exchange resin and separating the said 2-oxapropane.
4. The composition prepared according to the process of claim 3.

* * * * *